United States Patent [19]
Kogure et al.

[11] Patent Number: 4,804,657
[45] Date of Patent: Feb. 14, 1989

[54] PROCESS FOR PROTECTION OF BRAIN CELLS

[75] Inventors: Kyuya Kogure, Shakujii; Mitsuo Masaki, Chiba, both of Japan

[73] Assignee: Nippon Chemiphar Co., Ltd., Japan

[21] Appl. No.: 63,379

[22] Filed: Jun. 18, 1987

[30] Foreign Application Priority Data

Jun. 18, 1986 [JP] Japan .................................. 61-141593
Jan. 23, 1987 [JP] Japan .................................. 62-13876
May 30, 1987 [JP] Japan .................................. 62-136460

[51] Int. Cl.⁴ ..................... A61K 31/42; A61K 31/54; A61K 31/445
[52] U.S. Cl. .................................. 514/218; 514/317; 514/376
[58] Field of Search .................... 514/218, 317, 376

Primary Examiner—Stanley J. Friedman
Attorney, Agent, or Firm—Gerald J. Ferguson, Jr.

[57] ABSTRACT

A process for protection of brain cells which comprises orally or parenterally administering into a man suffering from ischemia or being susceptible to ischemia a 1,3-oxazolidin-2-one derivative having the formula:

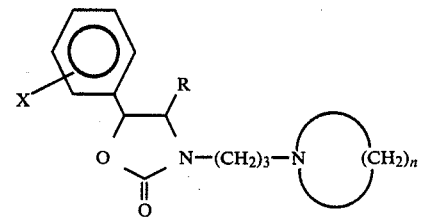

wherein R is a straight or branched chain alkyl having 3-8 carbon atoms, X is hydrogen, halogen, a lower alkyl or alkoxy, and n is 4, 5 or 6. Representative examples of the active component are (4S,5R)-4-(2-methylpropyl)-5-phenyl-3-(3-piperidinopropyl)-1,3-oxazolidin-2-one and (4S,5R)-4-(2-methylpropyl)-3-[3-(perhydroazepin-1-yl)-propyl]-5-phenyl-1,3-oxazolidin-2-one.

6 Claims, No Drawings

PROCESS FOR PROTECTION OF BRAIN CELLS

BACKGROUND OF THE INVENTION

1. Field of the Invention

The present invention relates to a process for protection of brain cells. 2. Description of Prior Art Recently, since a first aid treatment system has progressed, rate of death caused by cerebral infarction or cerebral hemorrhage is reduced. However, the reduced rate of death brings about another problem in that the cerebral infarction or cerebral hemorrhage causes dementia as an after effect. It is known that the cerebrovascular dementia is brought about through damage of brain cells which takes place in the course of ischemia caused by cerebral infarction or cerebral hemorrhage.

It has been recently confirmed that the damage of cells (or degeneration of brain cells) is caused not only as a direct result of the ischemia (that is, ischemic cell change), but also by a delayed effect (i.e., delayed neuronal death) which is observed even after the blood flow is recovered. Kirino et al. have reported in Brain Res. 239: 57–69 (1982) that when meriones unguiculstus is treated to ischemia for a short time at the forebrain and the blood flow is recovered, pyramidal cells are damaged and lost in the CA1 area of hippocampus after lapse of a certain period. This means that the brief ischemia causes the delayed neuronal damage. The hippocampus is the area of a brain where intellectual activity relating to emotion and memory is controlled. Accordingly, it is considered that damage of hippocampus is one reason to cause dementia.

Therefore, it has been earnestly desired to prevent or treat the dementia which may be observed after cerebral infarction and cerebral hemorrhage.

Regarding the above subject, Kirino et al. have further reported in Progress in Brain Research, vol. 63: 39–58 (1985) that pentobarbital having a cell membrane-stabilizing effect shows an effect of protection of brain cells and serves to markedly suppress the above-mentioned delayed neuronal damage.

As is described above, pentobarbital is of value for subsiding the delayed neuronal damage. However, since the action of pentobarbitol is not selective and the action of central nervous system is also strongly subsided, pentobarbital cannot be used in practice as a brain cell protective agent.

SUMMARY OF THE INVENTION

The present inventors have made study for a compound showing an effective brain cell protective action and now discovered that a 1,3-oxazolidin-2-one derivative having the formula (I):

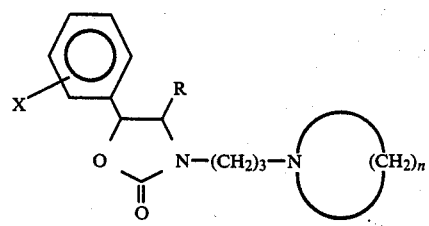

(I)

wherein R is a straight or branched chain alkyl having 3–8 carbon atoms, X is hydrogen, halogen, a lower alkyl or alkoxy, and n is 4, 5 or 6, shows an effective and selective brain cell protective action for a man suffering from ischemia or susceptable to ischemia.

DETAILED DESCRIPTION OF THE INVENTION

The 1,3-oxazolidin-2-one derivative having the formula (I) is already known to serve as a glutamate blocker and a rigidity releasing agent as described in West German provisional publication (OLS) No. P 3,519,261, and Japanese patent provisional publications No. 61(1986)-83170 and No. 61(1986)-205268.

In the formula (I), examples of the straight or branched chain alkyls having 3–8 carbon atoms which are represented by R include n-propyl, n-butyl, n-pentyl, n-hexyl, n-heptyl, n-octyl, 1-methylethyl, 1-methylpropyl, 2-methylpropyl, 1-methylbutyl, 2-methylbutyl, 3-methyl-butyl, 1-methylpentyl, 4-methylpentyl, 1-methylhexyl, 5-methylhexyl, 1-methylheptyl, 6-methylheptyl, 1,1-dimethylpropyl and 1-ethylbutyl.

The lower alkyl represented by X can be an alkyl groups having 1–6 carbon atoms such as methyl, ethyl, n-propyl and isopropyl. The lower alkoxy represented by X can be an alkoxy having 1–6 carbon atoms such as methoxy, ethoxy and n-propyloxy. The halogen represented by X can be chlorine, bromine or fluorine.

The compound of the formula (I) can be in the form of steric isomers such as cis-form (4RS, 5SR) and trans-form (4RS, 5RS) or in the form of various optical isomers such as (4R, 5S), (4S, 5R), (4R, 5R) and (4S, 5S). These isomers are included in the examples of the compounds of the formula (I).

The compound of the formula (I) can be prepared, for instance, by any one of the following processes.

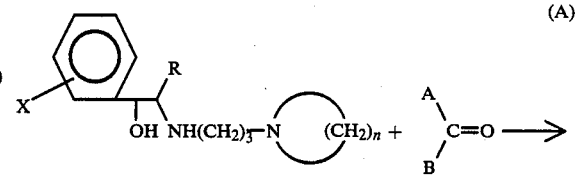

(A)

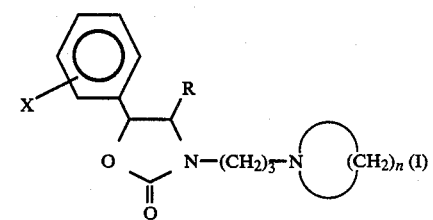

In the above equation, A is halogen or $C_1$–$C_3$ alkoxy, B is halogen, $C_1$–$C_3$ alkoxy, or trichloromethyloxy, and R, X and n have the same meanings as hereinbefore.

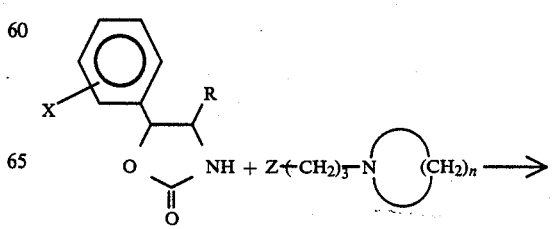

(B)

-continued

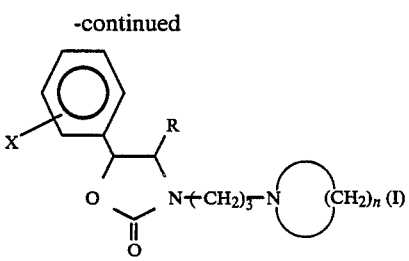

In the above equation, Z is halogen, tosyloxy or methyloxy, and R, X and n have the same meaning as above.

Representative examples of the compounds of the above-described formula (I) which serve as the active components in the pharmaceutical composition of the present invention include the following compounds:

Compound 1: (4RS,5SR)-4-(1-methylethyl)-5-phenyl-3-(3-piperidinopropyl)-1,3-oxazolidin-2-one;

Compound 2: (4RS,5SR)-4-(2-methylethyl)-5-phenyl-3-(3-piperidinopropyl)-1,3-oxazolidin-2-one;

Compound 3: (4RS,5SR)-4-(2-methylpropyl)-5-phenyl-3-(3-piperidinopropyl)-1,3-oxazolidin-2-one;

Compound 4: (4RS,5SR)-4-(1-methylethyl)-5-phenyl-3-(3-pyrrolidinopropyl)-1,3-oxazolidin-2-one;

Compound 5: (4S,5R)-4-(2-methylpropyl)-5-phenyl-3-(3-piperidinopropyl)-1,3-oxazolidin-2-one;

Compound 6: (4RS,5RS)-5-(3-methylphenyl)-4-(2-methylpropyl)-3-(3-piperidinopropyl)-1,3-oxazolidin-2-one;

Compound 7: (4RS,5SR)-5-(4-methoxyphenyl)-4-(2-methylpropyl)-3-(3-piperidinopropyl)-1,3-oxazolidin-2-one;

Compound 8: (4RS,5SR)-5-(4-fluorophenyl)-4-(2-methylpropyl)-3-(3-piperidinopropyl)-1,3-oxazolidin-2-one;

Compound 9: (4RS,5SR)-4-(3-methylbutyl)-5-phenyl-3-(3-piperidinopropyl)-1,3-oxazolidin-2-one;

Compound 10: (4RS,5SR)-4-hexyl-3-[3-(perhydroazepin-1-yl)propyl]-5-phenyl-1,3-oxazolidin-2-one; and Compound 11: (4S,5R)-4-(2-methylpropyl)-3-[3-(perhydroazepin-1-yl)propyl]-5-phenyl-1,3-oxazolidin-2-one.

Other valuable compounds having the formula (I) can be prepared in the manner described in the aforementioned Japanese patent provisional publications No. 61(1986)-83170 and No. 61(1986)-205268.

The pharmacological effect of subsiding the delayed neuronal disturbance or damage which is provided by the active compound of the formula (I) is shown by the following results of the pharmacological experiments in which the test compound was administered into a greater circulation system.

EXPERIMENT 1

Procedure of Experiment

Male Mongolian gerbils (approx. 12 week ages) were anesthetized. Their bilateral common carotide arteries at the neck were exposed, and occluded with clips for 5 minutes to cause ischemia at their forebrains. At the same time when the blood flow was recovered, fumarate of (4S,5R)-4-(2-methylpropyl)-3-[3-(perhydroazepin-1-yl)-propyl]-5-phenyl-1,3-oxazolidin-2-yl (hereinafter referred to as "active component A") at a dose of 40 mg/kg, pentobarbital (for control) at a dose of 40 mg/kg, or a physiological saline solution (which was employed as vehicle for the above test compound) was administered intraperitoneally.

After seven days, the treated animals were fixed by perfusion fixation which was carried out by introducing approx. 300 ml of 10% aqueous formalin solution into left ventricle at 120 cm.$H_2O$, and then immersed into the same solution for 48 hours. After the brains were dissected out and cut coronally into small blocks, the blocks were dehydrated and then embedded in paraffin according to the conventional manner. From the blocks, a metoic section of 5 μm thick was taken out at 1 to 1.5 mm posterior to the bregma. The specimen was then dyed with cresyl violet by Nissle dyeing method.

Similar specimen was also taken out of a normal group consisting of five animals which had not been subjected to the treatment for causing ischemia.

The specimen was observed by means of an optical microscope to measure number of pyramidal cells (i.e., neurons) contained in CA1 area of the specimen, as well as length of the pyramidal cell layer in the area. Then, number of pyramidal cells per 1 mm was calculated.

EXPERIMENTAL RESULTS

The results are set forth in Table 1.

TABLE 1

| Sample | Dosage (mg/kg,ip) | N | Number of CA1 neurons/mm |
|---|---|---|---|
| Physiological Saline | — | 10 | 3.50 ± 3.49 |
| Active Component A | 40 | 10 | 45.69 ± 25.10 |
| Pentobarbital | 40 | 10 | 51.44 ± 17.44 |
| Normal Group | — | 5 | 70.36 ± 17.49 |

As is shown in Table 1, decrease in pyramidal cell density at the CA1 area was observed in the saline-administered group. Enlarged microscopic observation further taught that there were present in the CA1 area atrophic pyramidal cells, cytoplasmic hyperchromatosis, karyolysis, and neuroglia cells produced.

In contrast, almost the same histological image as that of the normal group was observed in the active component A-administered group and the pentobarbital-administered group. The determination of number of pyramidal cells per 1 mm in the observed area indicates that these two compounds are apparently effective to subside the delayed neuronal disturbance. No statistically significant difference was observed on the number of pyramidal cells not only between the two compound-administered groups, but also between the compound-administered groups and the normal group. Also confirmed was that no statistically significant difference on the number of cells was present between the right and left hippocampuses.

Moreover, it was observed that the active component A-administered group showed no abnormal behaviour such as akinesia in traction test and rotarod test at a dose of 50 mg/kg, i.p., while the pentobarbital-administered group showed anesthetic conditions in the above tests even at a dose of 40 mg/kg, i.p.

EXPERIMENT 2

Procedure of Experiment

The experimental procedures of Experiment 1 were repeated except that the active component A was replaced with mesylate of (4S,5R)-4-(2-methylpropyl)-5- phenyl-3-(3-piperidinopropyl)-1,3-oxazolidin-2-yl (hereinafter referred to as "active component B") at a dose of 80 mg/kg.

Experimental Results

The results are set forth in Table 2.

TABLE 2

| Sample | Dosage (mg/kg,ip) | N | Number of CA1 neurons/mm |
|---|---|---|---|
| Physiological Saline (Control) | — | 8 | 5.2 ± 1.7 |
| Active Component B | 80 | 6 | 88.8 ± 22.7 |
| Pentobarbital | 40 | 8 | 101.1 ± 19.8 |

As is shown in Table 2, decrease in pyramidal cell density at the CA1 area was observed for the saline-administered control group.

In contrast, it was observed that the administration of the active component B showed prominent subsiding effect, which is significantly different from the effect observed in the control group. No statistically significant difference was observed on the effect not only between the two compound-administered groups, but also between the compound-administered groups and the normal group.

The above two pharmacological experiments reveal that 1,3-oxazolidin-2-one derivatives having the formula (I) show a brain cell protective action at a level similar to the action of pentobarbital. Further, the 1,3-oxazolidin-2-one derivatives of the formula (I) show essentially no anesthetic action, so long as they are administered at an ordinary dose level. Accordingly, the 1,3-oxazolidin-2-one derivatives of the formula (I) are effective to greatly subside delayed neuronal damage which is sometimes caused by cerebral infarction or cerebral hemorrhage, particularly for aged patients. Thus, the 1,3-oxazolidin-2-one derivatives of the formula (I) are effective to prevent dementia.

Further, the 1,3-oxazolidin-2-one derivatives of the formula (I) can be employed for obviating after-effect caused by temporary ischemia which may be brought about by temporary blood pressure reduction due to drowning, accident in anesthetic treatment, external wound, drugs, and the like.

Generally, it is known that a drug for treatment of brain should be passed through blood-brain barrier (BBB). It is understood that the 1,3-oxazolidin-2-one derivatives of the formula (I) easily pass through BBB because they are effective through the administration into the greater circularion system.

Accordingly, the active components of the invention, namely, 1,3-oxazolidin-2-one derivatives of the formula (I) can be administered through ordinary routes such as by oral administration and parenteral administration using a suppository or an injection.

Examples of the preparation forms for oral administration include tablets, capsules, powder, granules, and syrup. Examples of the preparation forms for parenteral administration include suppository and injection. In the formulation of these preparations, there can be used excipients, disintegrants, binders, lubricants, pigments, diluents and the like which are commonly used in the art. Examples of the excipients include glucose, lactose and microcrystalline cellulose. Examples of the disintegrants include starch and carboxymethylcellulose calcium. Examples of the lubricants include magnesium stearate and talc. Examples of the binders include hydroxypropylcellulose, gelatin and polyvinylpyrrolidone. Other additives can be also used.

The dose for injection generally is in the range of approx. 0.5 mg to 100 mg/day for an adult. The dose for oral administration generally is in the range of approx. 5 mg to 1,000 mg for an adult. These values are represented in terms of the amount of the physiologically active compound, namely the 1,3-oxazolidin-2-one derivative of the formula (I). These doses can be either increased or decreased depending upon the age and conditions of the patients.

The following examples further describe the present invention.

Reference Example 1

Preparation of fumarate of (4S,5R)-4-(2-methylpropyl)-3-[3-(perhydroazepin-1-yl)propyl]-5-phenyl-1,3-oxazolidin-2-one A mixture of 10.97 g (50 mmol) of (4S,5R)-4-(2-methylpropyl)-5-phenyl-1,3-oxazolidin-2-one, 13.26 g (62.5 mmol) of 1-(3-chloropropyl)perhydroazepin hydrochloride, 17.28 g (125 mmol) of powdery anhydrous potassium carbonate, and 100 ml of methyl ethyl ketone was heated under refluxing and stirring for 24 hours. After the heating was complete, the mixture was cooled and the precipitated insolubles were removed by filtration. The insolubles were washed with methyl ethyl ketone. The washings were combined with the filtrate (mother liquer) and concentrated under reduced pressure. The residue was dissolved in 70 ml of toluene, and washed with three 70 ml portions of toluene. The toluene was distilled off under reduced pressure. The residue was dissolved in 100 ml of ethanol and, after addition of 5.80 g (50 mmol) of fumaric acid, was heated for dissolution of the added fumaric acid. The resulting solution was allowed to stand overnight at room temperature. The precipitated crystals were collected by filtration, washed with three 20 ml portions of ethanol, and dried to give 19.31 g of crude crystals. The crude crystals were recrystallized from 290 ml of water to give 16.62 g of white crystalline fumarate of (4S,5R)-4-(2-methylpropyl)-3-[3-(perhydro-azepin-1-yl)propyl]-5-phenyl-1,3-oxazolidin-2-one, yield 70%).

m.p.: 171°–173° C.

$[\alpha]_D$: +11.7° (c 1.00, methanol).

$IR\nu_{max}^{KBr}$ cm$^{-1}$: 3460, 2930, 2620, 2560, 1740, 1720, 1685, 1610, 1460, 1420, 1240, 1165, 995, 980, 760, 745, 695.

REFERENCE EXAMPLE 2

Methanesulfonate of (4S,5R)-4-(2-methylpropyl)-5-phenyl-3-(3-piperidinopropyl)-1,3-oxazolidin-2-one In 12.4 ml of ice-water mixture was dissolved 12.38 g (62.5 mmol) of 1-(3-chloropropyl)piperidine hydrochloride. To the resulting solution was added 35 ml of 2N aqueous sodium hydroxide solution. The mixture was extracted with methyl ethyl ketone. The extract was washed with saturated aqueous sodium chloride solution, dried over anhydrous sodium sulfate, and filtered with suction. The collected insolubles were washed with methyl ethyl ketone. The filtrate and the washings were combined, and to the combined solution were added 17.25 g (125 mmol) of powdery anhydrous potassium carbonate and 10.96 g (50 mmol) of (4S,5R)-4-(2-methylpropyl)-5-phenyl-1,3-oxazolidin-2-one. The resulting mixture was heated under refluxing and stirring for 12 hours. The heated mixture was allowed to stand at room temperature. The mixture was then filtered with suction and the collected insolubles were washed with methyl ethyl ketone. The filtrate and the washings were combined and concentrated under reduced pressure. The residual pale yellow oil was dissolved in 100 ml of chloroform and, after addition of 100 ml of 2N HCl, was stirred for 30 min. The chloroform portion was recovered and this portion was washed with saturated aqueous sodium chloride solution, dried over anhydrous sodium sulfate, and filtered with suction. The collected insolubles were washed with chloroform. The filtrate and the washings were combined and placed under reduced pressure to distill off chloroform. The residual pale yellow oil was dissolved in 65 ml of a mixture of ethanol and ethyl acetate (1:10). To the resulting solution were added 4.80 g (50 mmol) of methanesulfonic acid and 4 ml of ethanol-ethyl acetate (1:10) mixture. The resulting mixture was stirred at room temperature. The precipitated crystals were collected by filtration, washed successively with a mixture of ethanol and ethyl acetate (1:20) and ethyl acetate, and dried to obtain 16.52 g of the desired product as a white crystalline product, yield 75%.

m.p.: 129°–131° C.

$[\alpha]_D$: +11.7° (c 5.00, methanol).

$IR\nu_{max}^{KBr}$ cm$^{-1}$: 3560, 3450, 2960, 2680, 1740, 1420, 1235, 1210, 1190, 1165, 1155, 1030, 1020, 770, 710.

EXAMPLE 1

A preparation in the form of pellets was prepared The pellets contained the following components per 100 mg.

| | |
|---|---|
| Active component | 10 mg |
| Lactose | 55 mg |
| Microcrystalline cellulose | 20 mg |
| Carboxymethylcellulose calcium | 10 mg |
| Hydroxypropylcellulose | 4 mg |
| Magnesium stearate | 1 mg |

EXAMPLE 2

A preparation in the form of gelatin hard capsules was prepared. One capsule contained 250 mg of the following components.

| | |
|---|---|
| Active component | 20 mg |
| Lactose | 110 mg |
| Starch | 90 mg |
| Talc | 5 mg |
| Microcrystalline cellulose | 23 mg |
| Magnesium stearate | 2 mg |

EXAMPLE 3

A preparation in the form of granules was prepared. The granules contained the following components per 1 g.

| | |
|---|---|
| Active component | 100 mg |
| Lactose | 450 mg |
| Corn starch | 400 mg |
| Hydroxypropylcellulose | 50 mg |

I claim:

1. A process for protecting brain cells from ischemia which comprises parenterally administering into a man suffering from ischemia or being susceptible to ischemia a 1,3-oxazolidin-2-one derivative having the formula:

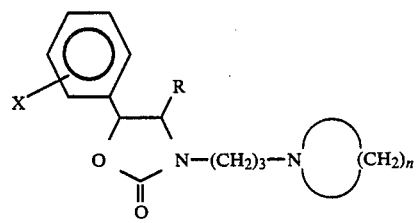

wherein R is a straight or branched chain alkyl having 3–8 carbon atoms, X is hydrogen, halogen, a lower alkyl or alkoxy, and n is 4, 5 or 6, at a dose of 0.5 to 100 mg per day.

2. The process as claimed in claim 1, wherein the 1,3-oxazolidin-2-one derivative is (4S,5R)-4-(2-methylpropyl)-5-phenyl-3-(3-piperidinopropyl)-1,3-oxazolidin-2-one.

3. The process as claimed in claim 1, wherein the 1,3-oxazolidin-2-one derivature is (4S,5R)-4-(2-methylpropyl)-3-[3-(perhydroazepin-1-yl)propyl]-5-phenyl-1,3-oxazolidin-2-one.

4. A process for protecting brain cells from ischemia which comprises orally administering into a man suffering from ischemia or being susceptible to ischemia a 1,3-oxazolidin-2-one derivative having the formula:

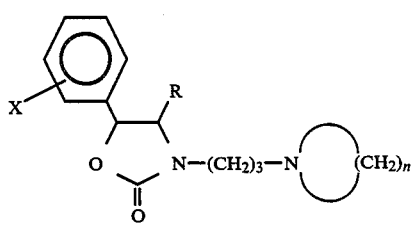

wherein R is a straight or branched chain alkyl having 3–8 carbon atoms, X is hydrogen, halogen, a lower alkyl or alkoxy, and n is 4, 5 or 6, at a dose of 5 to 1,000 mg per day.

5. The process as claimed in claim 4, wherein the 1,3-oxazolidin-2-one derivative is (4S,5R)-4-(2-methylpropyl)-5-phenyl-3-(3-piperidinopropyl)-1,3-oxazolidin-2-one.

6. The process as claimed in claim 4, wherein the 1,3-oxazolidin-2-one derivative is (4S,5R)-4-(2-methylpropyl)-3-[3-(perhydroazepin-1-yl)propyl]-5-phenyl-1,3,4-oxazolidin-2-one.

* * * * *